United States Patent [19]

Malmgren et al.

[11] 4,161,264

[45] Jul. 17, 1979

[54] FLUID METERING AND MIXING DEVICE HAVING INLET AND OUTLET VALVES

[76] Inventors: Arthur L. Malmgren, 386 NW. 112th. St., Seattle, Wash. 98177; Bryan E. Johnson, 21708 80th W., Edmonds, Wash. 98020

[21] Appl. No.: 807,425

[22] Filed: Jun. 17, 1977

[51] Int. Cl.$^2$ ............................................. B65D 37/00
[52] U.S. Cl. ..................................... 222/135; 222/183; 222/214; 222/440; 251/5
[58] Field of Search .................. 222/40, 61, 96, 103, 222/107, 135, 136, 137, 145, 183, 207, 212, 213, 214, 215, 308, 309, 334, 425, 434, 438–440; 251/5; 417/395, 510

[56] References Cited

U.S. PATENT DOCUMENTS

| | | | |
|---|---|---|---|
| 547,848 | 10/1895 | Davis | 222/440 X |
| 3,095,121 | 6/1963 | Doury et al. | 222/52 |
| 3,272,398 | 9/1966 | Drosman | 222/438 X |
| 3,308,898 | 3/1967 | Allen et al. | 222/214 X |
| 3,315,801 | 4/1967 | Lowry | 222/107 X |
| 3,599,525 | 8/1971 | Klann | 251/5 X |
| 3,727,804 | 4/1973 | Smith et al. | 222/334 X |
| 3,895,741 | 7/1975 | Nugent | 222/103 |
| 3,926,344 | 12/1975 | Bradley et al. | 222/145 |
| 4,042,153 | 8/1977 | Callahan et al. | 222/207 |

Primary Examiner—Robert J. Spar
Assistant Examiner—Fred A. Silverberg

Attorney, Agent, or Firm—Seed, Berry, Vernon & Baynham

[57] ABSTRACT

A metering device for delivering a fluid at a predetermined rate and a mixing device for delivering first and second fluids at a predetermined rate mixed in a predetermined ratio. The devices include a flexible fluid bladder having flexible inlet and outlet conduits, a flexible inlet conduit clamp tube overlying the inlet conduit, and a flexible outlet conduit clamp tube overlying the outlet conduit, all of which are positioned between a pair of abutting rigid plates having matching voids. As each of the clamp tubes are pressurized, the inlet or outlet conduits over which they lie are collapsed to prevent fluid flow therethrough. A valve system is provided for alternating between a fill cycle wherein the outlet conduit clamp tube is pressurized and the inlet conduit clamp tube is depressurized to allow fluid to flow into the fluid bladder, and a discharge cycle wherein the inlet conduit clamp tube is pressurized and the outlet conduit clamp tube is depressurized to allow fluid to flow from the fluid bladder. The rate at which the metering device delivers fluid is thus proportional to the product of the fluid bladder volume and the operating frequency of the valve system. A mixing device may be implemented by providing a second fluid bladder which is alternately filled and discharged into the outlet conduit of the first fluid bladder so that the fluids are mixed at a ratio corresponding to the volume of the first bladder to the volume of the second bladder.

6 Claims, 6 Drawing Figures

FLUID METERING AND MIXING DEVICE HAVING INLET AND OUTLET VALVES

BACKGROUND OF THE INVENTION

1. Field of the Invention

This invention relates to fluid handling devices and, more particularly, to devices for delivering fluid at a controlled rate and for mixing fluids in a controlled ratio.

2. Description of the Prior Art

In many fields it is necessary to deliver a single fluid at a precisely controlled rate or to deliver a predetermined mixture of fluid at a controlled rate. Pumps presently in use for these purposes are relatively expensive and somewhat complex. A more important disadvantage of conventional pumps when used in certain fields, such as the medical field, is the difficulty of sterilizing or cleaning such pumps. For example, in the field of dialysis treatment for kidney disease, a concentrated dialysate solution is mixed with water and dextrose before being directed to other dialysis equipment. It is extremely important that such equipment be sterile since the mixed dialysate can carry germs and infections to the patient, particularly during a peritoneal dialysis treatment. The medical field has generally solved the sterilization problem to a large extent by utilizing disposable, presterilized devices. However, it has not been possible to solve the sterilization problem of conventional dialysis pumps in this manner because their relatively high expense makes disposal after each use financially impractical.

SUMMARY OF THE INVENTION

It is an object of the invention to provide a relatively simple and inexpensive metering device capable of delivering a fluid at an accurately controlled rate.

It is another object of the invention to provide a relatively simple and inexpensive mixing device capable of delivering different fluids at a precisely controlled rate and mixing ratio.

It is still another object of the invention to provide a disposable metering and mixing device in which all fluid contacting portions are easily and inexpensively replaced.

It is a still further object of the invention to provide a mixing device which is easily adapted to mix a large number of fluids in any proportion.

These and other objects of the invention are provided by alternately filling and emptying a fluid chamber having a precisely controlled volume at a preset rate. The metering device utilizes a single fluid chamber so that the rate at which the fluid is delivered is proportional to the product of the volume of the chamber and the rate at which the chamber is filled and emptied. The metering device utilizes a plurality of fluid chambers emptying into a common discharge conduit so that the mixing ratio of the fluids correspond to the volume ratio of the respective fluid chambers receiving the fluids, and the mixed fluid is delivered at a rate proportional to the product of the sum of the volumes of the fluid chambers and the rate at which the chambers are filled and emptied. The flow of fluid into the chambers may be controlled by a unique valve system in which the inlet conduits and outlet conduits leading to and from the fluid chambers are flexible. Flexible clamp tubes overlay the inlet and outlet conduits between a pair of rigid plates so that pressurization of the clamp lines pinches off the adjacent inlet or outlet conduits. By alternately pressurizing and depressurizing the inlet conduit clamp tube and the outlet conduit clamp tube, the fluid chambers are alternately filled and emptied. The fluid chambers, inlet and outlet conduits, and clamp tubes may all be formed by flexible sheets bonded together. The sheets may be positioned between a pair of abutting plates having voids which mate with the fluid chambers and conduits formed in the sheets so that the fluid contacting portions of the metering and mixing device may be easily and inexpensively replaced by separating the plates and discarding the flexible sheets. A mixing device for precisely mixing any number of fluids in any proportion may be easily implemented by simply providing additional fluid chambers having a controlled volume.

DETAILED DESCRIPTION OF THE INVENTION

Figure 1:
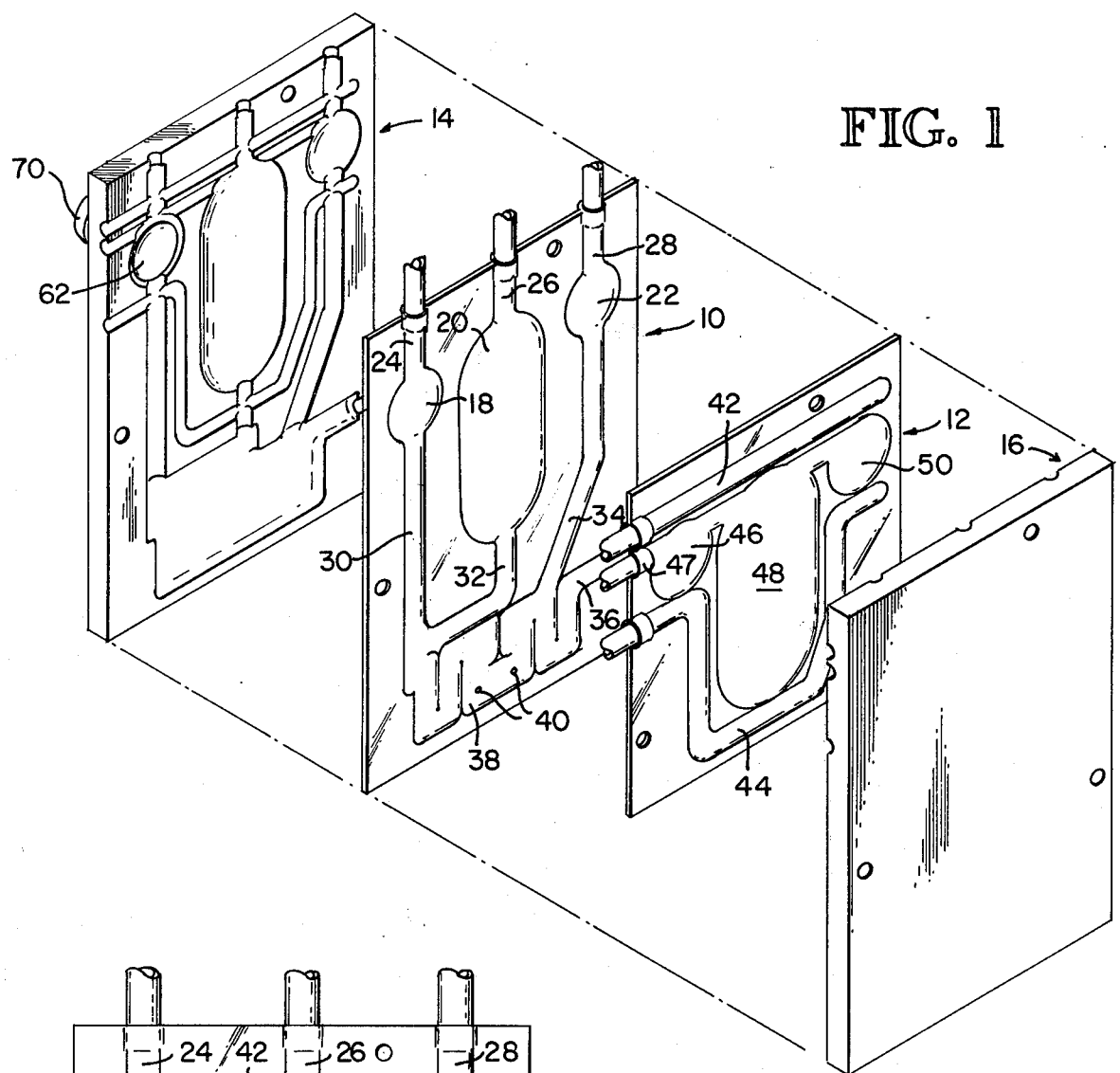
FIG. 1 is an exploded isometric view showing a mixing device for delivering a controlled mixture of three fluids at a precisely controlled rate.
Figure 2:
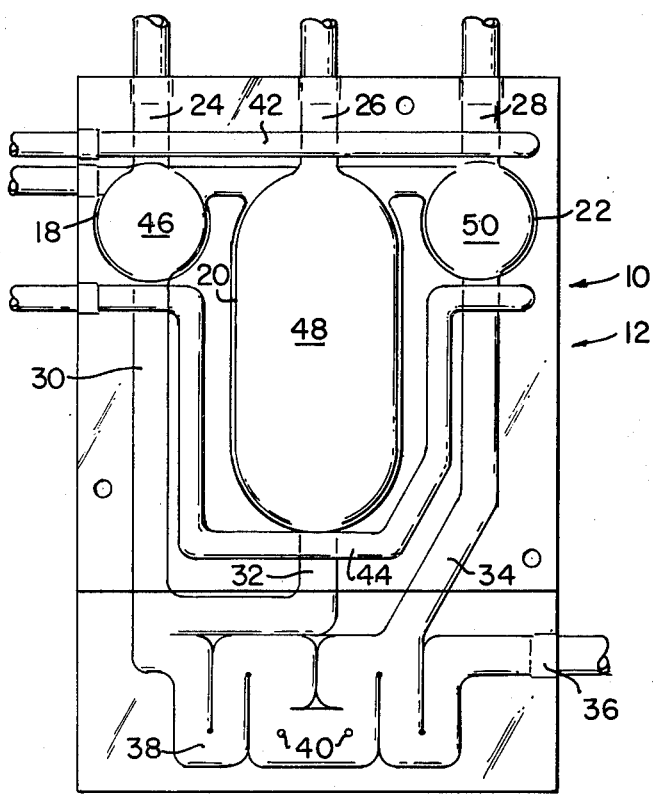
FIG. 2 is a plan view of the mixing device of FIG. 1.

A mixing device for mixing three different fluids at a controlled rate and in a predetermined ratio is illustrated in FIGS. 1 and 2. The device includes a fluid bag 10, a control bag 12 and a pair of plates 14, 16. The fluid bag 10 is preferably formed by bonding together two sheets of inexpensive flexible material, such as vinyl, at appropriate places to produce conduits and chambers so that the bag 10 may be inexpensively disposed of after each use. Where three different fluids are to be mixed, the fluid bag 10 will include a first fluid chamber 18, a second fluid chamber 20 and a third fluid chamber 22. The volume of each chamber 18-22 is proportional to the desired mixing ratio of the fluid received by the chamber. Inlet conduits 24, 26, 28 are connected to the tops of the fluid chambers 18, 20, 22, respectively, each of which have their upper ends connected to their respective fluid supplies. Similarly, the bottom portions of each fluid chamber 18, 20, 22 empty into outlet conduits 30, 32, 34, respectively. The outlet conduits 30-34 eventually empty into a common discharge conduit 36, but in certain fields it may be desirable to mix the fluids from two of the chambers 18, 20 before being mixed with the fluid from the third chamber 22. For example, in the field of dialysis a dialysate concentrate is diluted with water before being mixed with dextrose to form the final dialysate mixture. For the fluid bag 10 of FIG. 1 the dialysate concentrate is received in chamber 18 and water is received in chamber 20. The water and concentrate flow through outlet conduits 32, 30 and are combined in a mixing chamber 38 before being mixed with the dextrose flowing from chamber 22 through outlet conduit 34. The final dialysate mixture then flows from the discharge conduit 36. The mixing chamber 38 is provided with a pair of spaced apart electrodes 40 for measuring the resistivity of the diluted dialysate in order to insure the correct mixing concentration.

In order to accurately mix the fluids, the outlet conduits 30–34 are clamped and the inlet conduits 24–28 are unclamped as explained hereinafter thereby allowing the respective fluids to fill the fluid chambers 18–22. During the discharge cycle, the inlet conduits 24–28 are clamped and the outlet conduits 30–34 are unclamped thereby allowing fluid to drain from the chambers 18–22 where the fluids are mixed in the mixing chamber 38 and discharge conduit 36 in the proportions determined by the volume of each fluid chamber 18–22.

Although other devices may be used for blocking the inlet conduits 24–28 and outlet conduits 30–34 including electromechanical devices, a control bag 12 may be advantageously used for this purpose. The control bag 12, like the fluid bag 10, is preferably formed by bonding together a pair of flexible sheets at appropriate places in order to form chambers and conduits. The control bag 12 includes an inlet conduit clamp tube 42, an outlet conduit clamp 44 and three interconnected discharge chambers 46, 48, 50. As best seen in FIG. 2, the inlet conduit clamp tube 42 overlies all of the inlet conduits 24–28 directly above their respective fluid chambers 18, 20, 22. Similarly, the outlet conduit clamp tube 44 overlies all of the outlet conduits 30–34 directly beneath their respective fluid chambers 18, 20, 22. The discharge chambers 46, 48, 50 are similarly shaped and overlie the fluid chambers 18, 20, 22, respectively. The fluid bag 10 and control bag 12 are sandwiched between the rigid plates 14, 16, each of which have voids on their opposed surfaces which match the conduits and chambers in the fluid bag 10 and control bag 12. The plates 14, 16 abut each other with the bags 10, 12 therebetween and the chambers and conduits in the bags 10, 12 received by the voids in the plates 14, 16. The clamp tubes 42, 44 are alternately supplied with fluid at a higher pressure than the fluid in any of the conduits 24–28, 30–34. Since the fluids in the clamp tubes 42, 44 are at a substantially higher pressure than the pressure in the inlet conduits 24–28 or outlet conduits 30–34 and the spacing between the rigid plates 14, 16 within the voids is no more than the width of the clamp tubes 42, 44, the inlet conduits 24–28 are pinched off by the inlet conduit clamp tube 42 when the inlet conduit clamp tube is pressurized during the discharge cycle, and the outlet conduits 30–34 are pinched off by the outlet conduit clamp tube 44 when the outlet conduit clamp tube is pressurized during the fill cycle. During the discharge cycle the discharge chambers 46–50 are also pressurized thereby forcibly ejecting the respective fluids from the fluid chambers 18–22.

Although a mixing device having flexible fluid chambers and flexible conduits are illustrated in FIGS. 1 and 2, it is to be understood that rigid fluid chambers having inlet and outlet conduits which are alternately opened and closed may also be used. Similarly, rigid fluid chambers having flexible inlet and outlet conduits may be used, with the conduits being pinched off by either clamp tubes or by another means such as an electromechanical device.

The operation of the fluid mixing device can best be explained with reference to the schematic of FIG. 3. The clamp tubes 42, 44 and discharge chambers 46–50 are connected to a high pressure fluid source 52 through selectively actuated valves 54, 56, 58, respectively, and they are connected to a fluid return through bleeder valves 60, 62, 64, respectively. During the fill cycle valve 56 is opened thereby allowing the high pressure fluid in the outlet conduit clamp tube 44 to pinch off the outlet conduits 30–34. At the same time, the valves 54, 58 are closed allowing a pressure reduction in the inlet conduit clamp tube 42 through valve 60 and the discharge chamber tube 47 through valve 64. The respective fluids then flow into the fluid chambers 18, 20, 22 through inlet conduits 24, 26, 28, respectively, until all of the chambers are filled at the conclusion of the fill cycle. During the discharge cycle valve 54 is opened thereby allowing the high pressure fluid at 52 to flow into the inlet conduit clamp tube 42 and pinch off the inlet conduits 24–28. At the same time valve 56 is closed allowing a pressure reduction in the outlet conduit clamp tube 44 through valve 62 to open the outlet conduits 30–34 and allow fluid to drain from the fluid chambers 18–22. In order to maximize the speed at which the mixing device may operate, discharge chambers 46–50 may be used to forcible eject the fluid from the chambers 18–22. The discharge chambers 46–50 are also pressurized during the discharge cycle by opening valve 58 to connect the discharge chamber tube 47 to the high pressure source 52. Fluid flows from chambers 18, 20 through outlet conduits 30, 32, respectively, where they are combined combined in mixing chamber 38. The resistivity electrodes 40 monitor the resistivity, and hence concentration, of conductive fluids to insure correct mixing proportions. The fluid in the mixing chamber 38 is then combined with the fluid from chamber 22 flowing through outlet conduit 34, and the final mixture then flows from the discharge conduit 36. It is thus apparent that for each fill and discharge cycle, fluids occupying the volume of the respective fluid chambers 18–22 are combined at the discharge outlet 36. Thus, the mixing proportions of the fluids in the chambers 18–22 are equal to the proportion of the volume of the respective chambers to the sum of the volumes of the chambers 18–22. Similarly, the rate at which fluid is discharged from the discharge outlet 36 is equal to the product of the sum of the volumes of the chambers 18–22 and the frequency at which the fill and discharge cycles occur.

Figure 4:
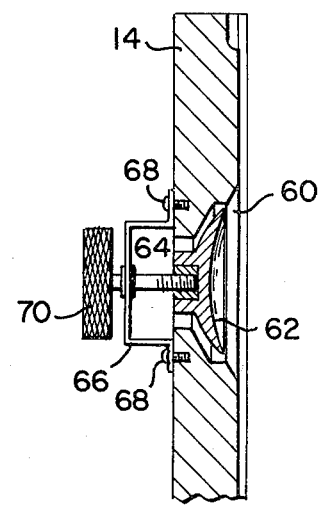
FIG. 4 is a cross sectional view taken along the line 4—4 of FIG. 1 illustrating a device for altering the mixing ratio of the mixing device of FIG. 1.

The volume of each fluid chamber 18–22 is generally determined by the volume of the matching voids in the plates 14, 16. Thus the volume of the chamber, and hence the mixing proportion of the fluid received by the chamber, may be adjusted by adjusting the size of the void which receives the fluid chamber. One embodiment of a device for performing this function is illustrated in FIG. 4. The plate 14 contains an aperture 60 which receives a cup-shaped member 62 having an outwardly dished surface for contacting the fluid chamber 18. The cup-shaped member 62 is threaded onto the end of a shaft 64 which is rotatably mounted on a bracket 66 secured to the outer face of the plate 14 by screws 68. A knob 70 is secured to the outer end of the shaft 64. The cup-shaped member 62 is moved toward and away from the fluid chamber 18 thereby decreasing and increasing its volume by rotating the knob 70.

Figure 5:
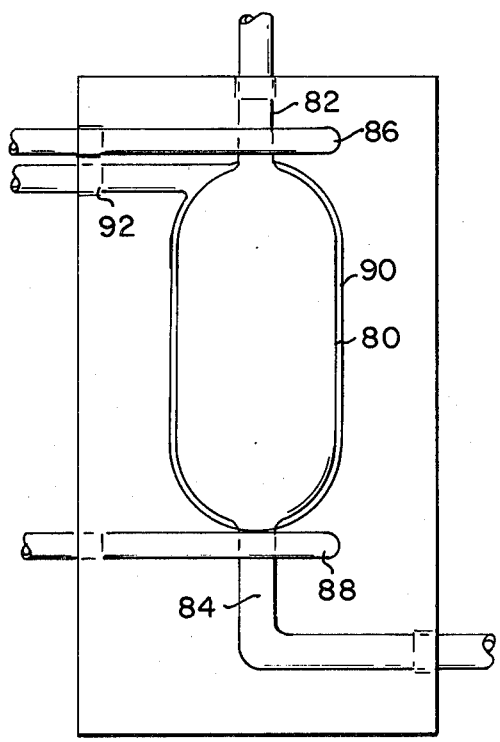
FIG. 5 is a plan view of a metering device for delivering a fluid at a controlled rate.

As mentioned previously, the rate at which the fluid is discharged from the mixing device is proportional to the product of the sum of the volumes of the mixing chambers and the rate at which the fluids in the chambers are discharged. Thus a mixing device having two or more fluid chambers also serves as a metering device for discharging fluid at a predetermined rate. Where it is desired to merely discharge a single fluid at a predetermined rate, a single fluid chamber may be used. A metering device using this principle is illustrated in FIG. 5. The device includes a single fluid chamber 80 receiving fluid at its upper end through an inlet conduit 82 and discharging fluid at its lower end through outlet conduit 84. A control bag placed adjacent the fluid bag includes an inlet conduit clamp tube 86, an outlet conduit clamp tube 88 and a discharge member 90 selectively receiving pressurized fluid through a discharge chamber tube 2. During the fill cycle the outlet conduit clamp tube 88 is pressurized and the inlet conduit clamp tube 86 and discharge chamber 90 are depressurized to allow fluid to flow into the fluid chamber 80 through inlet conduit 82. When the chamber 80 has been filled, fluid is discharged therefrom in a discharge cycle in which the inlet conduit clamp tube 86 is pressurized to prevent fluid flow into the fluid chamber 80, the outer conduit clamp tube 88 is depressurized to allow fluid to flow from the fluid chamber 80 through the outlet conduit 84, and the discharge chamber 90 is pressurized through the discharge chamber tube 92 to forcibly eject fluid from the fluid chamber 80. The rate at which fluid is discharged through the outlet conduit 84 is proportional to the product of the volume of the fluid chamber 80 and the rate at which the fluid chamber 80 is filled and emptied.

Figure 3:
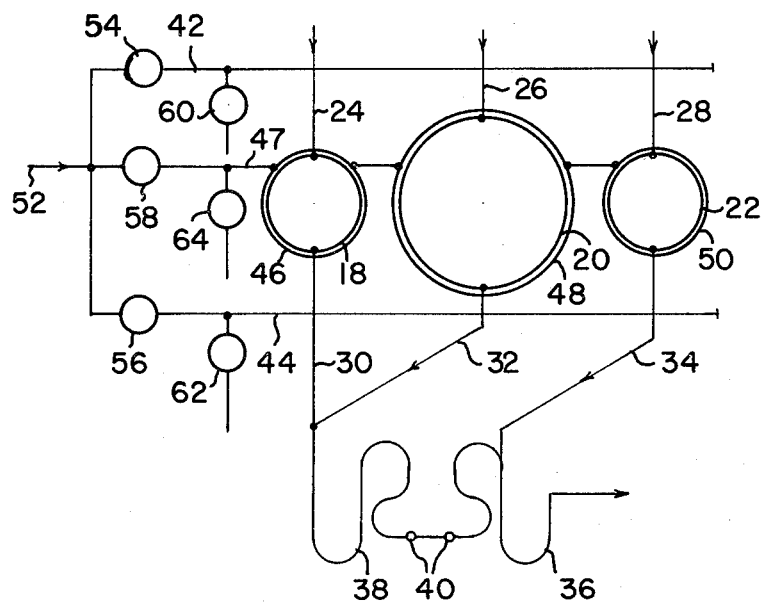
FIG. 3 is a schematic of the mixing device of FIG. 1 illustrating the external valving arrangement for pressurizing and depressurizing the clamp tubes during the fill and discharge cycles.
Figure 6:
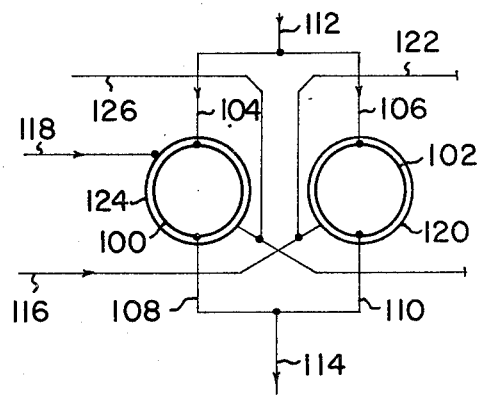
FIG. 6 is a schematic of a metering device for delivering a fluid at a controlled rate utilizing two fluid chambers which are alternately filled and emptied.

The flow of fluid from the mixing device illustrated in FIGS. 1–3 and the metering device illustrated in FIG. 5 is pulsating since fluid flows therefrom only during the discharge cycle. In order to achieve a smoother flow, a number of fluid chambers may be provided, and the operational sequence of each fluid chamber may be offset in phase so that as one fluid chamber is discharging fluid another fluid chamber is receiving fluid. One embodiment for performing this function is illustrated in FIG. 6. The device includes two fluid chambers 100, 102 each receiving fluid through respective inlet conduits 104, 106 and discharging fluid through outlet conduits 108, 110. The inlet conduits 104, 106 receive fluid from a common inlet tube 112, and the outlet conduits 108, 110 discharge fluid into a common outlet tube 114. During the fill cycle of fluid chamber 100 and the discharge of fluid from fluid chamber 102 clamp tube 116 is pressurized and clamp tube 118 is depressurized. Clamp tube 116 pinches off outlet conduit 108 and pressurizes a discharge chamber 120 thereby forcibly ejecting fluid from fluid chamber 102 through outlet conduit 110. At the same time, the inlet conduit 106 is pinched off by inlet clamp tube 122, and since tube 118 is depressurized, the discharge chamber 124 and the clamp tube 126 are depressurized thereby allowing fluid to flow into the fluid chamber 100 to inlet conduit 104. After fluid chamber 100 has been filled and fluid chamber 102 has been emptied, tube 118 is pressurized and tube 116 is depressurized thereby discharging fluid from fluid 100 and allowing fluid to flow into fluid chamber 102 in the same manner as previously stated. The resulting flow through the discharge conduit 114 is substantially more uniform than the single chamber variety of metering device.

The embodiments of the invention in which a particular property or privilege is claimed are defined as follows:

1. A device for metering a fluid at a predetermined flow rate, comprising:

a first fluid chamber having a predetermined volume;
a first set of flexible, elongated fluid inlet and outlet conduits communicating with said first fluid chamber;
a second fluid chamber having a predetermined volume;
a second set of flexible, elongated fluid inlet and outlet conduits communicating with said second fluid chamber;
a first flexible clamp tube having an externally accessible inlet end and a restricted terminating end, said first clamp tube overlying the inlet conduit of said first set and the outlet conduit of said second set;
a second flexible clamp tube having an extenrally accessible inlet end and a restricted terminating end, said second clamp tube overlying the outlet conduit of said first set and the inlet conduit of said second set;
a first pair of rigid surfaces spaced apart by the overlying portions of said first clamp tube and said inlet and outlet conduits by a fixed distance selected such that pressurization of said first clamp tube collapses the walls of the inlet conduit of said first set and the outlet conduit of said second set thereby preventing fluid flow into said first fluid chamber and from said second fluid chamber;
a second pair of rigid surfaces spaced apart by the overlying portions of said second clamp tube and said inlet and outlet conduits by a fixed distance selected such that pressurization of said second clamp tube collapses the walls of the outlet conduit of said first set and the inlet conduit of said second set thereby preventing fluid flow out of said first fluid chamber and also preventing fluid flow into said second fluid chamber; and
control means alternating between first and second cycles, said control means pressurizing said first clamp tube while depressurizing said second clamp tube during said first cycle thereby allowing fluid to fill said first fluid chamber and allowing fluid to drain from said second fluid chamber, and said control means depressurizing said first clamp tube while pressurizing said second clamp tube during said second cycle thereby allowing fluid to drain from said first fluid chamber and allowing fluid to fill said second fluid chamber such that the flow rate of fluid from said metering device is a substantially constant predetermined value.

2. The metering device of claim 1, wherein each of said fluid chambers is formed by a flexible fluid bladdder, and wherein said metering device further includes means for forcibly discharging fluid from said fluid bladders, comprising a flexible discharge bladder overlying each of said fluid bladders betwen a pair of rigid spaced apart surfaces, the discharge bladder for each fluid bladder communicating with the outlet conduit clamp tube for the other fluid bladder.

3. A device for metering a fluid at a predetermined flow rate, comprising:

a fluid chamber formed by a flexible fluid bladder;
fluid inlet and outlet conduits communicating with said fluid chamber;
inlet and outlet valve means for selectively opening and closing said inlet and outlet conduits, respectively;
control means alternating between fill and discharge cycles, said control means closing said outlet valve means while opening said inlet valve means during said fill cycle thereby allowing fluid to fill said fluid chamber through said inlet conduit, and said control means opening said outlet valve means while closing said inlet valve means during said discharge cycle thereby allowing fluid to drain from said fluid chamber through said outlet conduit such that the flow rate of fluid through said outlet conduit is substantially equal to the product of the volume of said fluid chamber and the operating frequency of said control means; and means for adjusting the flow rate of said metering device including a pair of rigid surfaces surrounding substantially the entire outer surface of the bladder, a portion of said rigid surfaces being adjustably spaced apart on opposite sides of the bladder and being independently operable from the inlet and outlet valve means to define a cavity having a volume less than the volume of said fluid bladder such that said bladder conforms to said rigid surface whereby the volume of said bladder, and hence said flow rate, may be adjusted by adjusting the spacing between said surfaces.

4. A device for mixing first and second fluids in a preset proportion, comprising:

a first bladder formed by a first pair of inexpensively disposable flexible sheets bonded together to form first and second fluid chambers, first and second inlet conduits connected to the top of said first and second fluid chambers, respectively, and first and second outlet conduits connected to the bottom of said first and second fluid chambers, respectively, and terminating in a common mixing conduit;

a second bladder formed by a second pair of flexible sheets bonded together to form an inlet conduit clamp tube adapted to overlie the first and second inlet conduits of said first bladder when said bladders are positioned adjacent each other and an outlet conduit clamp tube adapted to overlie the first and second outlet conduits of said first bladder when said bladders are positioned adjacent each other;

a pair of rigid plates having mating surfaces abutting each other, said plates having voids in said mating surfaces receiving said fluid chambers, inlet conduits, outlet conduits and clamp tubes; and control means alternating between fill and discharge cycles, said control means pressurizing said outlet conduit clamp tube while depressurizing said inlet conduit clamp tube during said fill cycle thereby allowing said first and second fluids to fill said first and second fluid chambers through said first and second inlet conduits, respectively, said control means depressurizing said outlet conduit clamp tube while pressurizing said inlet conduit clamp tube during said discharge cycle thereby allowing said first and second fluids to drain from said first and second fluid chambers through said first and second outlet conduits, respectively, such that said fluids are mixed in said preset proportion at a rate corresponding to the product of the volume of said fluid chambers and the operating frequency of said control means.

5. The mixing device of claim 4, further including a resistivity sensor disposed in said discharge conduit for providing an electrical indication of said preset proportion.

6. A pair of rigid plates positioned face-to-face adjacent each other, at least one of said plates having formed therein a cavity having a predetermined volume, inlet and outlet passages communicating with said cavity and inlet and outlet clamp passages overlying said inlet and outlet passages, respectively;

a flexible bladder positioned between said plates, said bladder forming a fluid chamber positioned within said cavity and having a volume at least as great as the volume of said cavity such that said fluid chamber conforms to the shape of said cavity and has a volume determined by the volume of said cavity, said bladder further forming inlet and outlet tubes communicating with said fluid chamber and positioned, respectively within said inlet and outlet passages;

flexible inlet and outlet clamp tubes positioned, respectively, in said inlet and outlet passages such that said inlet and outlet clamp tubes overlie said inlet and outlet tubes, respectively; and control means alternating between fill and discharge cycles, said control means pressurizing said outlet clamp tube while depressurizing said inlet clamp tube during said fill cycle thereby allowing fluid to fill said fluid chamber through said inlet tube, and said control means depressurizing said outlet clamp tube while pressurizing said inlet clamp tube during said discharge cycle thereby allowing fluid to drain from such fluid chamber through said outlet tube such that the flow rate of fluid through said outlet tube is substantially equal to the product of said predetermined volume and the operating frequency of said control means.

* * * * *